United States Patent
Liu et al.

(10) Patent No.: US 8,183,220 B2
(45) Date of Patent: May 22, 2012

(54) DOUBLE-EFFECTIVE VACCINE VECTOR AGAINST FOOT-AND-MOUTH DISEASE VIRUS (FMDV), METHODS OF PREPARING AND USING THE SAME

(75) Inventors: Jixing Liu, Lanzhou (CN); Bin Yang, Lanzhou (CN); Xi Lan, Lanzhou (CN); Xiangping Yin, Lanzhou (CN); Yinmei Bai, Lanzhou (CN); Xiaorong Han, Lanzhou (CN); Xuerui Li, Lanzhou (CN); Baoyu Li, Lanzhou (CN); Yuping Fang, Lanzhou (CN); Zhiyong Li, Lanzhou (CN)

(73) Assignee: Lanzhou Veterinary Research Institute Chinese Academy of Agricultural Sciences, Lanzhou (CN)

( * ) Notice: Subject to any disclaimer, the term of this patent is extended or adjusted under 35 U.S.C. 154(b) by 305 days.

(21) Appl. No.: 12/577,900

(22) Filed: Oct. 13, 2009

(65) Prior Publication Data

US 2010/0129402 A1    May 27, 2010

Related U.S. Application Data

(63) Continuation of application No. PCT/CN2008/000563, filed on Mar. 21, 2008.

(51) Int. Cl.
*A61K 48/00* (2006.01)
*C12N 15/113* (2010.01)
*C12N 15/42* (2006.01)
*C12N 15/85* (2006.01)

(52) U.S. Cl. ............ 514/44 A; 514/44 R; 424/216.1; 536/23.72; 536/24.5; 435/320.1

(58) Field of Classification Search .................. None
See application file for complete search history.

(56) References Cited

U.S. PATENT DOCUMENTS

2002/0193330 A1* 12/2002 Hone et al. .................. 514/44
2006/0293268 A1* 12/2006 Rieder et al. ................ 514/44

OTHER PUBLICATIONS

Yang et al (Journal of Gene Medicine 7:708-717, 2005).*
Rosas et al (Journal of General Virology 84:393-402, 2003).*

* cited by examiner

*Primary Examiner* — Mary E Mosher
(74) *Attorney, Agent, or Firm* — Matthias Scholl P.C.; Matthias Scholl

(57) ABSTRACT

A double-effective vaccine vector against foot-and-mouth disease virus having a bicistronic expression vector sequence, the bicistronic expression vector sequence is an antisense gene sequence capable of conjugating with 5' UTR of RNA of the foot-and-mouth disease virus genome and an intact sequence of VP1 structural protein gene of the foot-and-mouth disease virus. Animal experiments show that the vaccine vector provides double effects in terms of gene therapy and gene immunization for the prevention and treatment of foot-and-mouth disease in animals. Also provided are construction methods and methods of use of the vaccine vector.

7 Claims, 4 Drawing Sheets

FIG. 10

A. Commercialized bivalent vaccine
B. Double-effective vaccine
C. Buffer

Bar chart legend:
- before immunization
- 28 days after immunization
- 21 days after the second immunization Y-axis: OD570nm

FIG. 11

Construct: CMV promoter — EcoRI — 5' AsN — BamHI — IRES — SalI — VP1 — NotI — 3' UTR FMDV genome: 5' UTR — IRES — VP1 — 3' UTR — (A)n 5' AsN (412 nt) between AUG and AUG

SEQUENCE LISTING

<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: Synthetic amplification primer designed for AsN gene segment and VP1 structural protein gene of the foot-and-mouth disease virus -continued

```
<400> SEQUENCE: 1
gcgaattcat gccagcacgg caactttac                                        29

<210> SEQ ID NO 2
<211> LENGTH: 29
<212> TYPE: DNA
<213> ORGANISM: Artificial Sequence
<220> FEATURE:
<223> OTHER INFORMATION: Synthetic amplification primer designed for AsN
      gene segment and VP1 structural protein gene of the foot-and-mouth
      disease virus

<400> SEQUENCE: 2
ctagctagcg ttgggcctgg agtagaatg                                        29

<210> SEQ ID NO 3
<211> LENGTH: 34
<212> TYPE: DNA
<213> ORGANISM: Artificial Sequence
<220> FEATURE:
<223> OTHER INFORMATION: Synthetic amplification primer designed for AsN
      gene segment and VP1 structural protein gene of the foot-and-mouth
      disease virus

<400> SEQUENCE: 3
gcgtcgaccc accatgcacg cagaccacct ccac                                  34

<210> SEQ ID NO 4
<211> LENGTH: 28
<212> TYPE: DNA
<213> ORGANISM: Artificial Sequence
<220> FEATURE:
<223> OTHER INFORMATION: Synthetic amplification primer designed for AsN
      gene segment and VP1 structural protein gene of the foot-and-mouth
      disease virus

<400> SEQUENCE: 4
gcgcggccgc ttcacaggcg ccacaatc                                         28
```

DOUBLE-EFFECTIVE VACCINE VECTOR AGAINST FOOT-AND-MOUTH DISEASE VIRUS (FMDV), METHODS OF PREPARING AND USING THE SAME

CROSS-REFERENCE TO RELATED APPLICATIONS

Pursuant to 35 U.S.C. §119 and the Paris Convention Treaty, this application is a continuation of International Patent Application No. PCT/CN2008/000563, with an international filing date of Mar. 21, 2008, designating the United States, now pending, and further claims priority benefits to China Patent Application No. 200710103083.7, filed May 28, 2007. The contents of all of the aforementioned applications, including any intervening amendments thereto, are incorporated herein by reference.

BACKGROUND OF THE INVENTION

1. Field of the Invention

The invention relates to a vaccine vector and a method of preparing the same, and more particularly to a double-effective recombinant vaccine vector against foot-and-mouth disease virus, preparation method and method of use thereof.

2. Description of the Related Art

Almost all of the vaccines have different duration of periods for the production of effective antibodies, i.e. the immunity blank period. When the animals fall across the pathogenic microorganisms, prevalence of the disease will frequently occur in this period; on the other hand, inoculation of the vaccine to silently infected animals might cause severe clinic reactions, even death in a few cases. It is a problem in dire need of solving to rid the animals in the immunity blank period of the attacks by the pathogens and to prevent the animals in silent infection period from the occurrence of severe clinic reactions and even death.

SUMMARY OF THE INVENTION

In view of the above-described problem, it is one objective of the invention to provide a vaccine vector against O-type foot-and-mouth disease virus (FMDV) having the effects in terms of gene therapy and genetic immunization for the prevention and treatment of against foot-and-mouth disease virus.

It is another objective of the invention to provide a method of preparation of a vaccine vector against O-type foot-and-mouth disease virus (FMDV) having the effects in terms of gene therapy and genetic immunization for the prevention and treatment of the foot-and-mouth disease virus.

To achieve the above objectives, in accordance with one embodiment of the invention, provided is a vaccine vector against O-type foot-and-mouth disease virus (FMDV) having the effects in terms of gene therapy and genetic immunization for the prevention and treatment of the foot-and-mouth disease virus, comprising a bicistronic expression vector sequence comprising an antisense gene sequence capable of conjugating with 5' untranslated region (UTR) of RNA of the foot-and-mouth disease virus genome and an intact sequence of VP1 structural protein gene of the foot-and-mouth disease virus.

In a class of this embodiment, the bicistronic expression vector is pIRES, and the antisense gene sequence is a gene segment AsN of the foot-and-mouth disease virus.

In a class of this embodiment, the vaccine vector against the O-type foot-and-mouth disease virus (FMDV) is pAsN-IR-VP1.

In accordance with another embodiment of the invention, provided is a method of preparing a vaccine vector against O-type foot-and-mouth disease virus (FMDV) comprising reversely inserting a gene segment targeting FMDV 5'UTR into a first multiple clone site of a bicistronic expression vector, and forward inserting an intact gene of VP1 structural protein into a second multiple clone site of the bicistronic expression vector.

In a class of this embodiment, the first multiple clone site of the bicistronic expression vector is the multiple clone site A of pIRES, and the second multiple clone site of the bicistronic expression vector is the multiple clone site B of pIRES.

Based on the theory that antisense RNA can inhibit the translation of mRNA into proteins by binding to a normal sense mRNA, thereby inhibiting the replication of the virus, whereas the nucleic acid vaccine can induce effective cellular immunity and humoral immunity, thereby protecting the animals from the attack of specific pathogens, the invention has prepared a vaccine vector against O-type foot-and-mouth disease virus (FMDV) having both effects in terms of gene therapy and genetic immunity. Before an effective antibody is produced after introduction of a nucleic acid vaccine of the invention, by means of the inhibition of the antisense nucleic acid on pathogens silently infected and intruding before vaccination on the animals, the vaccine resists the harm done by the pathogens, thereby solving the problem due to immunity blank period. In addition, after the production of specific antibody, the vaccine immunity effect is strengthened with double effects of the neutralization of the pathogen as well as the inhibition of the antisense nucleic acid on it. Through following experiments, e.g., transfection of cells using the double-effective vector, screening of the stable clones, amplification and reproduction of the clones, the preparation of the vaccine and measurement of the antibodies in the immunized animals thereafter, as well as potent toxin attacks etc, relatively ideal experimental results have been obtained.

The double-effective recombinant plasmid was transfected into BHK-21 cells by means of a liposome-mediated method, assays such as RT-PCR etc showed that the antisense RNA of the double-effective recombinant plasmid was transcripted in the cells; virus inhibition test and the test measuring the decrease of plaques showed the 5' AsN scripton can effectively inhibit the replication of the homologous virus. Inoculating the virus after transfection for 24 h, the inhibition rate reached higher than 60%. Sandwich ELISA as well as indirect immunofluorescence assays showed that the VP1 structural protein gene of the double-effective recombinant plasmid was stably expressed in BHK-21 cells, and it had a certain level of bioactivity.

After repetitive screening of the cell clones transfected with the double-effective recombinant plasmid of the invention by means of the G418 screening strategy, cell strain with stable resistance was obtained. RT-PCR assay showed that the recombinant plasmid can steadily pass down to the future generation in BHK-21 cells.

After large scale extraction of the double-effective vaccine vector of the invention, mice were immunized with the vaccine, and their blood was sampled. LBP-ELISA analysis of the mouse blood samples showed that the double-effective vaccine can stimulate the animal to produce antibody. The antibody titer in different batches of the mice was between 1:32 and 1:64 in 3 weeks after second immunization; MTT assay showed that the double-effective vaccine vector can induce the proliferative response of the spleen T lymphocytes in the animal body. The production of effective antibody in the immunized mice and the proliferative response of the T lymphocyte verified that the double-effective vaccine vector has genetic immunization effect. 6-12 h after the immunization of suckling mice with the double-effective vaccine vector, the mice were attacked with 20-100 TCID50 potent poison, the results showed that the double effect plasmid can protect the sucking mice from the FMDV potent poison attack, the protection rate reached 50%-83%, this testified the gene therapy effect of the double-effective vaccine vector.

BRIEF DESCRIPTION OF THE DRAWINGS

The invention is described hereinafter with reference to accompanying drawings, in which:

FIG. 10 is a proliferation image of mouse spleen lymphocytes according to one embodiment of the invention; and FIG. 11 is a schematic diagram of the construction of a double-effective vaccine vector according to one embodiment of the invention.

DETAILED DESCRIPTION OF THE EMBODIMENTS

Below is the further illustration of this invention with the embodiments. These embodiments are totally used for illustrative purpose. Various modifications to the models and methods of the invention can be made by those skilled in the art on the basis of their understanding of the true scope and spirit of the invention, these modifications will fall within the scope of the invention.

Example 1

Construction of Double-Effective Vaccine Vector pAsN-IR-VPI

1. Preparation of Target Gene:

The amplification primers designed for the 5' AsN segment and VP1 structural protein gene were:

```
AsN1:
5'-gcgaattcatgccagcacggcaactttac-3';  (856-873),
    (SEQ ID NO. 1) Eco RI AsN2:
5'-ctagctagcgttgggcctggagtagaatg-3;  (1200-1219),
    (SEQ ID NO. 1) Nhe I XP1:
5'-gcgtcgacCcaccatgcacgcagaccacctccac-3';
    (3247-3264),  (SEQ ID NO. 1) Sal I XP2:
5'-gcgcggccgcttcacaggcgccacaatc-3'.  (3865-3882),
    (SEQ ID NO. 1) Not I
```

In the primers, to the upstream of AsN1 and XP1 an initiation codon ATG was introduced, to 3' end of their downstream a termination codon was introduced, meanwhile to the upstream of XP1 the elements such as Kozak sequence etc. were introduced.

Figure 1:
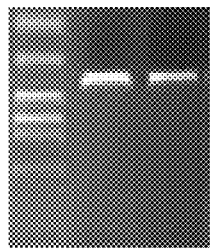
FIG. 1 is a schematic view of a product of 5' AsN PCR according to one embodiment of the invention.
Figure 2:
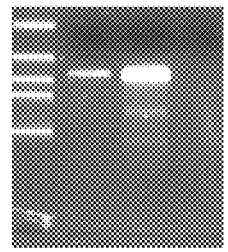
FIG. 2 is a schematic view of a product of VP1 PCR according to one embodiment of the invention.

Foot-and-mouth disease virus OMIII strain (which was a strain separated, preserved, passed down and proliferated in the BHK-21 cells by the Lanzhou Veterinary Research Institute, Chinese Academy of Agricultural Sciences; this foot-and-mouth disease virus OMIII strain might also be substituted with other foot-and-mouth disease virus strain or analogous strains thereof obtained by the prior art) was used as template to be amplified (The amplification procedure for AsN gene segment: predenaturing at 94° C. for 5 min; 94° C. for 1 min; 58° C. for 45 s; 72° C. for 50 s.; after 30 cycles, extension at 72° C. for 8 min; and the amplification procedure for VP1 gene: predenaturing at 94° C. for 5 min; 94° C. for 1 min; 60° C. for 1 min; 72° C. for 1 min, after 30 cycles, extension at 72° C. for 8 min). The PCR products after amplification were shown in FIGS. 1 and 2, respectively.

2. Construction of Double-Effective Vaccine Vector

5' AsN gene segment as well as the gene of the structural protein VP1 were subcloned into the multiple cloning sites A and B of bicistronic expression vector pIRES (obtained from Invitrogen), respectively, to construct FMDV double-effective vector pAsN-IR-VP1 (The promoter of the bicistronic expression vector was CMV; the terminator was polyA).

Figure 3:
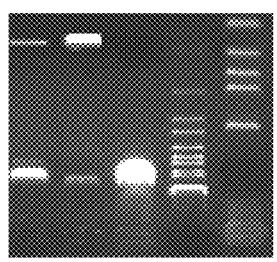
FIG. 3 is an image of enzymatic digestion and PCR identification of the recombinant plasmid pAsN-IR according to one embodiment of the invention.
Figure 4:
FIG. 4 is an image of enzymatic digestion and PCR identification of a recombinant plasmid pAsN-IR-VP1 according to one embodiment of the invention.

The construction of bicistronic expression vector as described herein comprises the steps of:
1) Doubly-digesting target gene 5' AsN with enzymes EcoRI and NheI, and purifying the recovered target segment;
2) Doubly-digesting bicistronic expression vector pIRES with enzymes EcoRI and NheI to obtain a linearized vector;
3) Ligating the aforementioned products at the cohesive ends using a T4 DNA ligase;
4) Transforming *E. Coli.* (JM109) with the ligation product by means of conventional technique, screening the bacteria on ampicillin resistant agar plate, and separating plasmids from the picked clones;
5) Identifying the plasmids using techniques of enzymatic digestion and PCR amplification (As shown in FIG. 3) and positive recombinant plasmid pAsN-IR was obtained;
6) Doubly-digesting the target gene VP1 with enzymes Sal I and Not I to yield a target gene having cohesive ends;
7) Doubly-digesting the pAsN-IR plasmid obtained in the former procedure with enzymes EcoRI and NheI to obtain a linearized vector; and
8) Ligating the target gene having cohesive ends and the linearized vector, transformating, picking out clones, separating plasmid, and identifying with enzymatic digestion, PCR amplification, and DNA sequencing etc. to yield pAsN-IR-VP1. (As shown in FIG. 4).

Example 2

Test of the Expression of Double-Effective Vaccine Vector pAsN-IR-VP1 In Vitro

1. Transfection of BHK-21 Cells with Double-Effective Vaccine Vector pAsN-IR-VP1
   1) Preparation of the plasmid for transfection: following the manual of the kit for preparing ultra pure plasmid DNA, plasmid pAsN-IR-VP1 was separated under aseptic conditions. The result of agarose gel electrophoresis verified the correct plasmid was obtained, and then the content and purity of the DNA were determined with a spectrophotometry;
   2) Transfection of the cells: BHK-21 cells were cultured at 37° C. using DMEM culture medium containing 6% calf serum in an incubator containing 5% $CO_2$, when the cells grew full, healthy cells were picked out, digested with trypsin, counted in a haemocyte counting plate, subsequently inoculated into a 6 well-incubation plate, and cultured overnight in an antibiotic-free complete medium at 37° C.;
   3) A liposome (Lipofectamine™ 2000) suspension was added into DMEM culture medium and mixed thoroughly, and the resultant mixture was incubated at room temperature; meanwhile the cell culture medium of step 2) was removed using a pipette, and the cells were washed once with DMEM culture medium;
   4) When the cell fusion rate reached 70%-80%, they were transfected under the mediation of Lipofectamine™ 2000. DNA/liposome complex was added into each petri dish, incubated in a 5% $CO_2$ incubator, and then the culture medium containing the DNA/liposome complex was removed with a pipette. After 4 h of cell transfection, antibiotic-free DMEM containing 5% serum was supplemented to maintain normal growth of the cells. MEM culture medium containing same concentration of Lipofectamine™ 2000 was added into the control well.
   5) After the transfection of the liposome, the transfected cells were used to screen stable resistant cell strain and detect the expression of double-effective plasmid in vitro.

Figure 5:
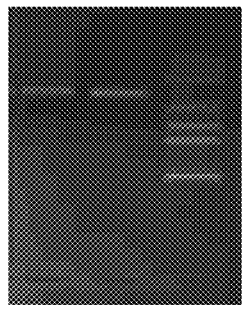
FIG. 5 is an image of RT-PCR assay of the RNA transcription of a double-effective vaccine vector according to one embodiment of the invention (1, 2: RT-PCR amplification of 5' AsN in cell sap at 24 and 48 h after transcription, respectively; 3: DL2000 Marker)
Figure 6:
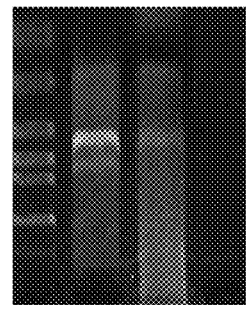
FIG. 6 is an image of RT-PCR assay of the RNA transcription of a double-effective vaccine vector according to one embodiment of the invention (1: DL2000 Marker. 2: amplification of VP1 in the stable cell sap; 3: amplification of VP1 in the DNA separated from BHK cells; 4: negative control)
Figure 7:
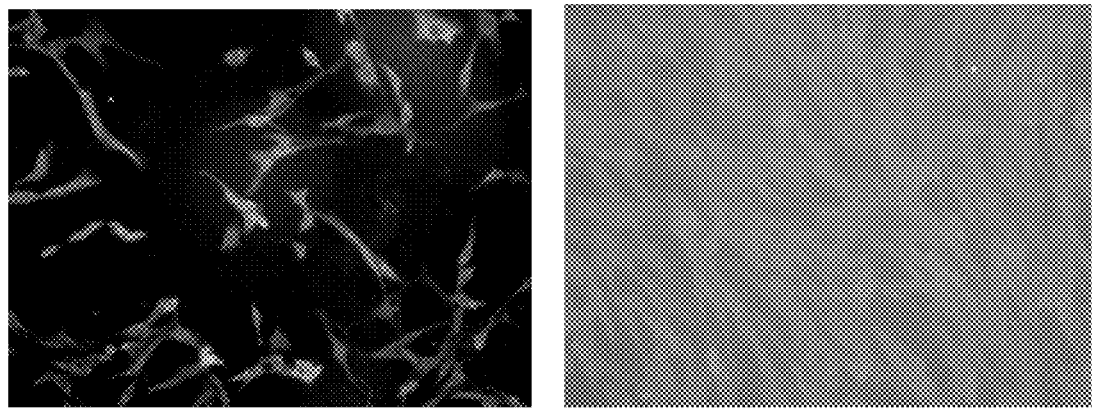
FIG. 7 is an image of transfected BHK-21 cells stained by an indirect immunofluorescence according to one embodiment of the invention (A: Transfected with double-effective plasmid; B: non-transfected cells)
Figure 8:
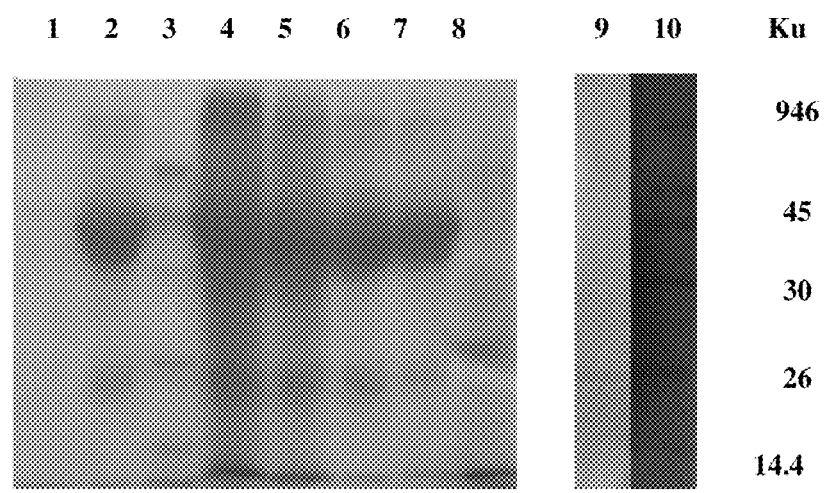
FIG. 8 is an image of results obtained with SDS-PAGE and Western-blot assays according to one embodiment of the invention (1: Supernatant of the cell culture; 2: Supernatant of the cell lysate after transfection; 3 and 10: Low-molecular protein Marker; 4, 5, 6, 7, and 9: lysate of the cells after transfection; 8: BHK-21 control)
Figure 9:
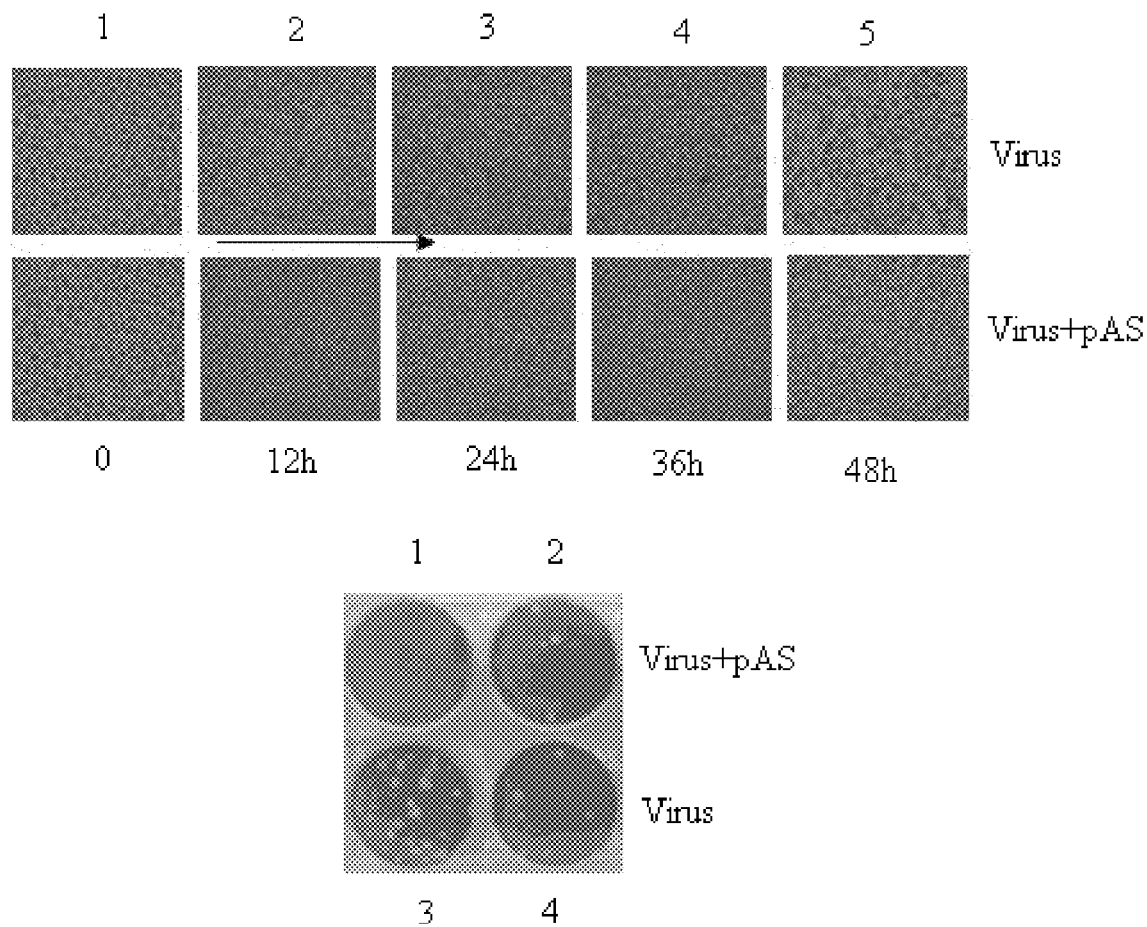
FIG. 9 is an image of pathological changes of the cells in virus inhibition experiments and the results of testing decrease of plaques according to one embodiment of the invention ((A) First row, IBRS-2 cells were inoculated with FMDV OMIII with amount of 100 TCID$_{50}$: 1. IBRS-2 control; 2, 3, 4 and 5: at 12, 24, 36, 48 h after inoculation of the virus to IBRS-2 cells, respectively; Second row: at 24 h after the double-effective plasmid transfect, the cells were inoculated with FMDV OMIII with amount of 100 TCID$_{50}$: 1. IBRS-2 control; 2, 3, 4 and 5: at 12, 24, 36, 48 h after the transfected cells were inoculated with the virus, respectively. (B) Decrease of the plaques: 1. IBRS-2 cell control; 2. The formation of the plaques at 24 h after the double-effective plasmid transfected, the cells were inoculated with FMDV OMIII with amount of 10 TCID$_{50}$; 3 and 4: The formation of the plaques inoculated with FMDV OMIII with amount of 100 TCID$_{50}$ and 10 TCID$_{50}$, respectively)

2. Detection of the Expression of the Double-Effective Vaccine Vector In Vitro
   1) Detecting the transcription of antisense RNA segment in the recombinant plasmid pAsN-IR-VP1 in the cells using RT-PCR technique, and the results is shown in FIG. 5;
   2) Virus inhibition test was carried out using BHK-21 cells transiently transfected with pAsN-IR-VP1 or using the screened stable cell line to evaluate the inhibition effect of the antisense RNA scripton on the virus production. The main operations were as follows:
      a) 24 h after transfection of cells with pAsN-IR-VP1, inoculating the cells with FMDV OMIII in the amount of 100 TCID50/0.1 mL, after adsorption for 1 h, the supernatant was discarded, the cells were washed with DMEM twice, and DMEM containing 4% FBS was added to continue culturing; and
      b) The cell supernatant was sampled at different times after infection. The virus toxic potencies were measured on BHK-21 cells collected at different times (Bigeriego et al., 1999; Gutie'rrez et al., 1993). Average values of virus inhibition rate obtained from three independent virus inhibition tests were calculated, using the cell clone transfected with blank plasmid as a control group, the inhibition rate PI on the virus production was obtained.
   3) The inhibition of antisense RNA scripton on the virus production can be more directly detected by means of plaque decrease test using the BHK-21 cells transiently transfected with pAsN-IR-VP1 or using the screened stable cell line. The main procedure was as follows:
      a) Culturing the IBRS-2 cells using the conventional method;
      b) The cells were washed with sterilized PBS solution, inoculated with FMDV OMIII in the amount of 100 TCID50/0.1 mL (200 µL/well, 6-well plate), and placed in a $CO_2$ incubator;
      c) 1 h later, 2 mL/well of the overlay culture medium (one aliquot with 2×MEM, one aliquot with 1.2% agar) was added into the wells, and allowed to stand still for 24-48 h;
      d) The culture medium was discarded using a pipette, and an ice fixation fluid (50% acetone+50% methanol) was added and fixed at −20° C. for 10 min;
      e) Approximately 2 mL of a crystal violet staining solution was added, staining at room temperature for 30 min; and
      f) The cells were rinsed with distilled water, dried naturally, and then the plaques were counted to obtain the virus toxic potencies. The experimental results are shown in FIG. 9.
   4) The expression of the gene of the structural protein VP1 in the BHK-21 cells were assayed using double antibody sandwich ELISA, the main operations were as follows:
      a) Recombinant double effective plasmid pAsN-IR-VP1 were used to transfect BHK-21 cells, continuing culture;
      b) Cells were collected after 24 and 48 h respectively, washed with 0.01M PBS (pH 7.4) and digested with trypsin, after centrifugation, the supernatant was discarded; the precipitated cells were lysed with lysate and subsequently centrifugalized, and the supernatant was assayed with ELISA; and
      c) Assay of the antigen with double antibody sandwich ELISA: 96-well ELISA Plate was embedded with rabbit FMDV positive serum (1:1000) and stood overnight at 4° C., after blocked with horse serum, the FMDV antigen, the cell lysate containing transfection plasmid pAsN-IR-VP1, and the cell lysate as blank control were serially diluted in a gradient of 2×, and 2 wells were allocated for every dilution. These solutions were incubated at 37° C. for 1 h, washed, and then FMDV guinea pig positive antiserum (1:800) was added. The resultant solution was allowed to react at 37° C. for 1 h, washed, and then HRP-rabbit anti guinea pig IgG (1:2000) was added. The resultant solution was further allowed to react at 37° C. for 1 h, and then a substrate of OPD-$H_2O_2$ was added and allowed to continue reacting at 37° C. for 15 min. Finally, the reaction was terminated with a termination solution, and OD value was determined at a wavelength of 492 nm.

5) The detection of the expression of structural protein gene VP1 in BHK-21 cells by means of indirect immunofluorescence test, the main operations were as follows:

a) Cover slips in the culture dishes with a density of the growing transfected cells more than 90% were collected, washed with 0.01 mol/L PBS buffer (pH 7.4), fixed for 30 min, and washed with PBS buffer;

b) Rabbit FMDV positive serum (1:1000) was added drop-wise, incubated for 30 min in a humid chamber, and FITC-goat anti rabbit IgG (1:40) was added; and c) The cells were stained for 30 min, rinsed with PBS buffer, dried naturally, blocked with glycerol, observed under fluorescent microscope with photographs taken. The test results were show in FIG. 7.

Example 3

Screening and Identification of Stable Resistant Cell Strain

The process of screening stable resistant cell strain comprises the following operations:

1) determination of concentration of G418: the optimal amount of G418 was obtained through establishment of cell mortality curve, i.e. the cells was firstly diluted to 1000 cell/mL, 100 μL of the cell suspension was added into each well of the 24-well plate containing culture medium, the concentrations of G418 in the wells were diluted to 12 levels of 0, 100, 200, 300, 400, 500, 600, 700, 800, 900, 1000, and 1100 μg/mL. The cells were continued culturing for 3-4 weeks, with the culture medium updated every 3-4 d, the cell mortality curve was established based on the minimal G418 concentration at which the cells died completely, which is commonly around 400-800 μg/mL. The screened G418 concentration was one level higher than the aforementioned minimal G418 concentration. The concentration of G418 in the well in which the BHK-21 cells died completely was selected as the optimal for screening stable resistant BHK-21 cells. The final screened concentration was 500 μg/mL, and half of the screened concentration was used for maintaining the culture.

2) Screening of the stable resistant cell strain: after growing close to fusion, the transfected BHK-21 cells were passed down with density 1:4, and cultured. When the cell concentration reached 50%-70%, the culture medium was discarded and substituted with 500 μg/mL G418 culture medium for screening using non-transfected normal cells as control. When most of the control cells died, the screening solution was once more replaced, in which the concentration of G418 can be 250 μg/mL. About 10-20 d later, formation of resistant clones can be observed. Cells were counted under a microscope when the clones grew larger. The monoclonal cell island was enclosed with a cell cannula, and subsequently the cells were digested. The digested cells were transferred into 96-well plates for culturing, each of the wells were added with 100 μL of complete medium and placed into a $CO_2$ incubator for 24 h, and then 100 μL of G418 screening solution having working concentration was subsequently added. According to the aforementioned conditions, the culture medium was updated every 3-4 d of culturing. In some of the wells visible cell colonies can be observed after 14-21 d. The colonies were picked out, transferred to a 6-well plate for culturing, and when growing healthily, transferred to culture flasks for culturing.

3) RT-PCR identification of stable resistant cell strain: The BHK-21 cells having been screened using G418 for several times were digested with trypsin, subsequently centrifuged at 4000 r/min for 5 min, after discarding the supernatant, the precipitation was lysed with a cell lysate, frozed and melted for several cycles, centrifuged once more and amplified the supernatant by means of PCR technique; meanwhile, DNA separated from the BHK-21 cells was also amplified using PCR technique to confirm the existence of target gene. The amplified gene was purified, ligated with Teasy vector, and transformed. The plasmid was separated from the plaques, identified with PCR as well as enzymatic digestion. The positive clones were sequenced for analyzing the variation of the sequence.

The results of the experiments: through repetitive G418 screening of the cell clone transfected with double-effective plasmid pAsN-IR-VP1, the stable resistant BHK-21 cell strain was obtained. RT-PCR assay as well as plaque decrease experiment showed that the double-effective plasmid can stably pass down in BHK-21 cells.

Example 4

Animal Immunizing Test

1) Large scale extraction of plasmid pAsN-IR-VP1 was performed using E.Z.N.A Fastfilter Endo-free Plasmid Maxi Kit, OMEGA, following the operation manual of the kit. The content and purity of the DNA were measured with a spectrophotometer.

2) 24 mice of 5-6 days old were randomly divided into 4 groups (6/group), i.e., a first immunized group with double-effective plasmid pAsN-IR-VP1, a second immunized group with double effective plasmid pAsN-IR-VP1+lidocain, an inactivated vaccine group, and a control group of buffer solution. 4 weeks after the first immunization, the mice were booster-immunized once. 4 weeks after the second immunization, the mice were executed. The group treated with plasmid+lidocain was injected lidocain (4 mg/Kg body weight) one week before injecting plasmid so as to increase the absorption of the plasmid DNA by the cells. Blood was collected via caudal veins at different times after immunization.

3) After the serum was isolated, the production of antibodies in mice was assayed with LBP-ELISA technique, and the results are shown in Table 1.

TABLE 1

Assay of VP1 specific antibody

| Groups | Days after 1st immunization | | Days after 2nd immunization | | |
|---|---|---|---|---|---|
| | 21 | 28 | 14 | 21 | 28 |
| Double-effective plasmid | 1:2 | 1:2 | 1:4 | 1:8 | <1:4 |
| Double-effective plasmid + Lidocain | 1:4 | 1:8 | 1:32 | 1:64 | 1:32 |
| O-type inactivated vaccine | 1:4 | 1:12 | 1:90 | 1:60 | <1:16 |
| PBS | <1:2 | <1:2 | <1:2 | <1:2 | <1:2 |

4) Mice spleen lymphocytes were collected before immunizing the mice, 28 d after first immunization and 21 d after second immunization, respectively, T lymphocyte proliferation test was performed by means of MTT method.

A suspension of the mice lymphocyte was prepared under sterilized condition, and the cell suspension was diluted to a single-cell suspension having a concentration $2 \times 10^7$ cells/mL. 50 μL of the diluted suspension was added into each well of a 96-well cell-culture plate, followed by 50 μL PHA solution (concentration: 500 μg/mL). Each test sample with cell suspension was triplicate, another sample was set for the control, in which only RPMI 1640 culture solution was added with no cell suspension, and other conditions were the same as that in the test sample. The cells were cultured at 40° C. for 45 h in an atmosphere of 5% $CO_2$ under saturated humidity. Each well was added with 10 μL of MTT solution (5 mg/mL), continued to culture for 3 h. After being taken out from the incubator, 100 μL of 10% SDS-0.01 mol/L HCl solution was added into each well, mixed uniformly, and placed into a cell incubator for 2 h. The OD value of the test sample of each well was measured at the wavelength of 570 nm using the control well sample for zero adjustment. The result was obtained using the average values from triplicate cell suspension samples. The results were shown in FIG. 10.

The result of the experiment: after the immunization of the mice with the double-effective vaccine pAsN-IR-VP1, LBP-ELISA assay of the blood samples collected from the mice showed that the double-effective vaccine pAsN-IR-VP1 was capable of stimulating the animal body to produce antibodies. 3 weeks after the second immunization, the antibody potency can reach 1: 32-1:64. MTT test showed that the double-effective plasmid pAsN-IR-VP1 can induce the proliferation of the spleen T lymphocytes in the animal body. Both the production of effective antibodies in the immunized mice and the proliferation of the spleen T lymphocytes verified the gene immunity of the double-effective plasmid pAsN-IR-VP1.

Example 5

The Poison Attack Test on Sucking Mice

The vaccine produced with the double-effective plasmid pAsN-IR-VP1 separated on large scale from recombinant bacteria was used to immunize animals, or the vaccine produced from the screened stable BHK-21 cells containing double-effective plasmid pAsN-IR-VP1 was used to immunize animals.

Sucking mice of clean grade aged 3-4 days was used to measure the $LD_{50}$ value of the FMDV OM III. Subsequently, 24 sucking mice were selected to perform the poison attack test. The sucking mice were randomly divided into 4 groups, i.e., Control group 1, Control group 2, Immunized group 1, and Immunized group 2. The two immunized groups were immunized with the double-effective plasmid pAsN-IR-VP1, and the two control groups were administered PBS buffer. When testing, two immunized groups were immunized firstly by inoculating 100 μg per animal with the double-effective plasmid pAsN-IR-VP1 into the back muscles, after 6-12 h, the group 1 was hypodermically inoculated 100 μL of OM III virus into the back of the sucking mice with the dosages of 20 $LD_{50}$ and the group 2 with the dosages of 100 $LD_{50}$ (i.e., $10^{-4}$ and $10^{-3}$ amount of the virus, respectively). The two control groups were injected with PBS and then were attacked with the virus with the same dosages as that of two test groups respectively. The animals were observed for 10 d, and the protection rates of the sucking mice were calculated. The results were shown in Table 2.

TABLE 2

Results of sucking mouse toxin attack experiment

| Groups | Virus dosage (100 μL) | Mortality | Protection rate |
|---|---|---|---|
| Control group 1 | $10^{-3}$ (100TCID$_{50}$) | 6/6 | 0 |
| Immunized group 1 | $10^{-3}$ (100TCID$_{50}$) | 3/6 | 50% |
| Control group 2 | $10^{-4}$ (10TCID$_{50}$) | 6/6 | 0 |
| Immunized group 2 | $10^{-4}$ (10TCID$_{50}$) | 1/6 | 83% |

The experimental results showed that the protection rate obtained by using the double-effective plasmid pAsN-IR-VP1 of the invention can reach 50%-83%, which showed that the double-effective vaccine of this invention possesses significant effect of gene therapy on FMDV.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A double-effect immunizing vector against O-type foot-and-mouth disease virus at least comprising a bicistronic expression vector sequence, wherein said bicistronic expression vector sequence comprises an antisense gene sequence capable of hybridizing with 5' UTR of RNA of foot-and-mouth disease virus genome and an intact sequence of VP1 structural protein gene of said foot-and-mouth disease virus.

2. A double-effect molecular therapeutic against foot-and-mouth disease virus, comprising a therapeutically effective dose of the vector of claim 1 and a pharmaceutically acceptable excipient.

3. A method of treatment against foot-and-mouth disease virus comprising administering to a patient in need thereof a pharmaceutical composition comprising said vector of claim 1.

4. The vector of claim 1, wherein the antisense gene sequence is prepared using gene sequences of SEQ ID NO.1 and SEQ ID NO.2 as amplification primers.

5. The vector of claim 1, wherein the VP1 structural protein gene is prepared using gene sequences of SEQ ID NO.3 and SEQ ID NO.4 as amplification primers.

6. An immunogenic vector against O-type foot-and-mouth disease virus comprising an expression vector pIRES into which inserted are: an antisense gene sequence capable of hybridizing with 5'UTR of RNA of foot-and-mouth disease virus genome and an intact sequence of VP1 structural protein gene of said foot-and-mouth disease virus.

7. A method of constructing the vector of claim 6, the method comprising cloning said antisense gene sequence into a first multiple cloning site of the expression vector pIRES, and cloning said VP1 structural protein gene into a second multiple cloning site of the expression vector pIRES.

* * * * *